(12) United States Patent
Esnouf

(10) Patent No.: US 9,694,118 B2
(45) Date of Patent: Jul. 4, 2017

(54) PORTABLE VACUUM DEVICE

(75) Inventor: Philip Stuart Esnouf, Hawthorn (AU)

(73) Assignee: Construct Medical Pty, Ltd., Victoria (AU)

( * ) Notice: Subject to any disclaimer, the term of this patent is extended or adjusted under 35 U.S.C. 154(b) by 250 days.

(21) Appl. No.: 13/883,295

(22) PCT Filed: Nov. 3, 2011

(86) PCT No.: PCT/AU2011/001408
§ 371 (c)(1),
(2), (4) Date: Jul. 18, 2013

(87) PCT Pub. No.: WO2012/058720
PCT Pub. Date: May 10, 2012

(65) Prior Publication Data
US 2013/0289504 A1    Oct. 31, 2013

(30) Foreign Application Priority Data

Nov. 3, 2010 (AU) ................................ 2010904892

(51) Int. Cl.
*A61M 1/00* (2006.01)
*A61M 27/00* (2006.01)
*A61F 13/00* (2006.01)
*A61B 17/50* (2006.01)
*A61M 13/00* (2006.01)

(52) U.S. Cl.
CPC ........ *A61M 1/0031* (2013.01); *A61M 1/0001* (2013.01); *A61M 1/005* (2014.02); *A61M 1/0052* (2014.02); *A61M 1/0076* (2013.01)

(58) Field of Classification Search
CPC ........ A61M 1/00; A61M 13/02; A61M 27/00; A61F 13/00; A61B 17/50
See application file for complete search history.

(56) References Cited

U.S. PATENT DOCUMENTS

| 4,319,570 A | 3/1982 | Grane |
| 4,790,818 A | 12/1988 | DeLuca et al. |
| 5,383,851 A | 1/1995 | McKinnon, Jr. et al. |
| 2005/0027252 A1 | 2/2005 | Boukas |

(Continued)

FOREIGN PATENT DOCUMENTS

| CN | 2058850 U | 7/1990 |
| CN | 2746914 Y | 12/2005 |

(Continued)

OTHER PUBLICATIONS

International Search Report issued Jan. 17, 2012 in PCT/AU2011/001408 filed Nov. 3, 2011.

*Primary Examiner* — Tatyana Zalukaeva
*Assistant Examiner* — Ilya Treyger
(74) *Attorney, Agent, or Firm* — Banner & Witcoff, Ltd.

(57) ABSTRACT

A portable vacuum device including: a source of liquefied gas; a gas operated vacuum generator having a vacuum inlet; a valve for controlling flow of gas from the source to the vacuum generator; a suction tube having proximal and distal ends; a collection container having an outlet coupled to the vacuum inlet of the vacuum generator and an inlet coupled to the proximal end of the suction tube, the arrangement being such that when said valve is opened the vacuum generator creates a vacuum in the container and at the distal end of the suction tube.

13 Claims, 1 Drawing Sheet

(56) References Cited

U.S. PATENT DOCUMENTS

2005/0261642 A1* 11/2005 Weston .................. 604/313
2006/0271018 A1   11/2006 Korf
2010/0241026 A1    9/2010 Boukas
2012/0157911 A1    6/2012 Rooks et al.

FOREIGN PATENT DOCUMENTS

| CN | 201692380 U    |   | 1/2011  |
|----|----------------|---|---------|
| JP | 61-177648      |   | 11/1986 |
| JP | H08141089 A    |   | 6/1996  |
| JP | 2008119237 A   |   | 5/2008  |
| WO | 03/009766 A1   |   | 2/2003  |
| WO | WO 03/009766   | * | 2/2003  |
| WO | 2008/049029 A2 |   | 4/2008  |
| WO | 2012058720 A1  |   | 5/2012  |

* cited by examiner

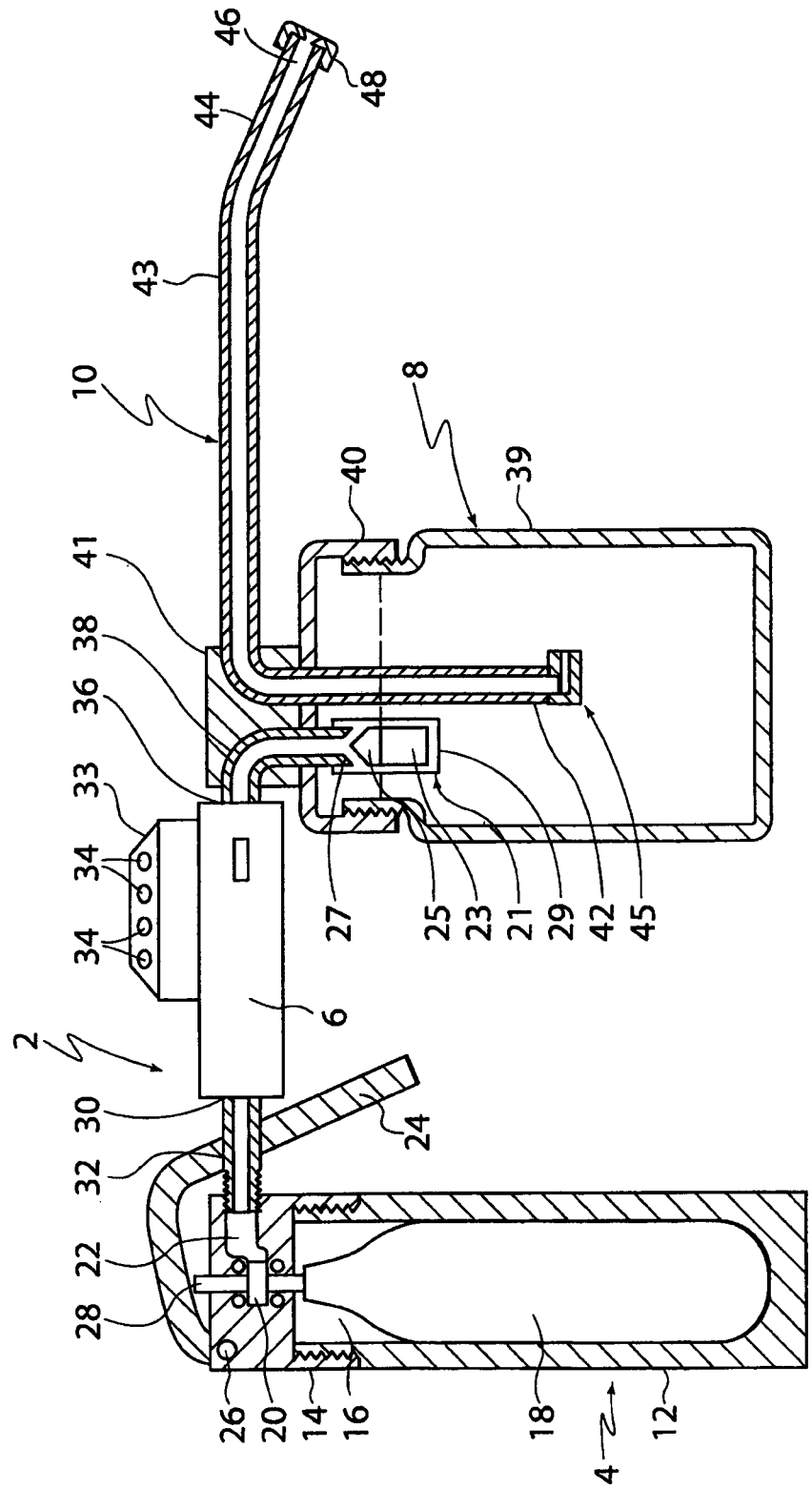

PORTABLE VACUUM DEVICE

This application is a U.S. National Stage application of co-pending PCT application PCT/AU2011/001408 filed Nov. 3, 2011, which claims the priority of Australian application 2010904892, filed Nov. 3, 2010, each application being incorporated by reference in their entirety.

This invention relates to a portable vacuum device.

More particularly, the invention relates to a portable hand held vacuum device which can be used in first aid and medical applications especially for clearing the airway of a person who is suffering from trauma, injury or other medical condition in which the person's airway is or could be blocked.

There have been proposals in the past to make portable suction devices. Battery driven vacuum pumps, which are capable of producing a vacuum level of −40 kPa, are not really practical because the devices would be bulky and would have relatively short battery life. Such devices would also be quite expensive to make and maintain.

There have been proposals to use aerosol type cans in order to produce gas flows which can be directed through venturis in order to create vacuums for portable suction devices. Generally speaking these devices are of limited utility because they would have difficulty achieving the required levels of vacuum and would have limited operating time. U.S. Pat. Nos. 6,845,542 and 5,989,360 are examples of these types of device. Some of these require heating to the can in order to function which is cumbersome and expensive. Other proposals such as U.S. Pat. Nos. 6,094,778 and 5,924,166 propose the use of compressed air. These devices would have similar drawbacks.

As indicated above, all of the proposed devices have the drawback that they would produce limited levels of vacuum which would probably be insufficient for medical applications.

There have also been proposals to use the oxygen from oxygen cylinders which are normally provided in ambulances or the like as the source gas for creating vacuum. The oxygen can be discharged through a venturi to produce a workable suction device suitable for medical applications but owing to the size of the oxygen cylinder is not really portable or handheld. Further, this technique has the distinct disadvantage that substantial amounts of oxygen needs to be dissipated in order to create the required suction and this is undesirable because normally the oxygen supply is limited and is usually required to assist the oxygenation of a patient whose breathing ability is impaired.

The object of the present invention is to provide a portable vacuum device which at least partly overcomes the drawbacks of the prior art.

According to the present invention there is provided a portable vacuum device including:

a source of liquefied gas;

a gas operated vacuum generator having a vacuum inlet;

a valve for controlling flow of gas from said source to the vacuum generator;

a suction tube having proximal and distal ends;

a collection container having an outlet coupled to the vacuum inlet of the vacuum generator and an inlet coupled to the proximal end of the suction tube, the arrangement being such that when said valve is opened the vacuum generator creates a vacuum in the container and at the distal end of the suction tube.

The invention also provides a portable vacuum device including:

a source of liquefied gas;

a gas operated vacuum generator having a vacuum inlet;

a valve for controlling flow of gas from said source to the vacuum generator;

a suction tube having proximal and distal ends;

a collection container having an outlet coupled to the vacuum inlet of the vacuum generator and an inlet coupled to the proximal end of the suction tube, the arrangement being such that when said valve is opened the vacuum generator creates a vacuum in the container and at the distal end of the suction tube;

characterised in that the vacuum at the distal end of the tube is less than −40 kPa.

Preferably, the pressure at the distal end of the tube is in the range −60 kPa to −40 kPa.

Preferably further, liquefied gas is carbon dioxide.

Preferably further, the device includes a pressure chamber within which can be located a cartridge containing liquid carbon dioxide.

Preferably further, the capacity of the cartridge is such that the vacuum generator can be operated for a total time in the range from 1 to 15 minutes.

Carbon dioxide cartridges are widely available having a capacity of 16 grams. By suitable adjustment of the orifice sizes in the vacuum generator, the device may operate for a minute or more but even with this relatively modest total time of operation, the device is still useful because it normally needs to be used only intermittently. It is preferred, however, that a larger cartridge would be used say having a capacity in the range from 40 to 88 grams so that a proportionately larger operating time is available.

The advantages of the invention are that it can be made cheaply so that it is a device which is disposable. In other words it can be made and/or supplied as a single use device. The cartridge containing the liquefied carbon dioxide can be of a commercially available type and this further reduces costs of production.

The vacuum generator can also be of a multiple venturi type which is capable of producing high levels of vacuum.

The invention also provides a method of providing a portable hand-held suction device, the method including the steps of:

(i) providing a chamber for a canister of liquid carbon dioxide;

(ii) providing means for selectively passing carbon dioxide from the canister to a vacuum generator;

(iii) coupling an inlet of the vacuum generator to a container;

(iv) providing a suction tube having proximal and distal ends, the proximal end being in fluid communication with the interior of the container whereby a user can selectively release carbon dioxide from the canister thereby causing a vacuum in the container and at the distal end of the suction tube.

The invention will now be further described with reference to the accompanying drawing, in which:

FIG. 1 is a schematic cross-sectional view through a portable vacuum device of the invention.

FIG. 1 shows a portable vacuum device 2 of the invention. It includes a main body assembly 4, vacuum generator 6, collecting container assembly 8 and suction tube 10. The main body assembly 4 includes a housing 12 which is screw threaded to a cap 14. Within the housing 12 and cap 14 is a pressure chamber 16. The size of the pressure chamber 16 is selected such that it can snugly receive a $CO_2$ cartridge 18. As the chamber 16 is subjected to the pressure of $CO_2$ released from the cartridge 18, the housing 12 and cap 14 need to be of relatively robust construction. The cap 14 includes a valve 20 for controlling flow of carbon dioxide from the chamber 16 to an outlet port 22. The assembly 4 includes an operating lever 24 which is pivoted to the cap by means of pivot pin 26. In operation, rotation of the lever 24 (clockwise as shown in FIG. 1) causes downward displacement of an operating spindle 28 which opens the valve 20 and releases $CO_2$ into the outlet port 22. Release of the lever 24 permits the spindle 28 to rise and the valve 20 to close off escape of carbon dioxide from the chamber 16.

The vacuum generator 6 has an inlet port 30 which is coupled by means of a screw threaded connector 32 to the outlet port 22. The vacuum generator 6 has an exhaust outlet (not shown) which is coupled to an exhaust filter 33 having outlet openings 34. It is preferred that the filter 33 is a medical grade airway filter, the function of which is to remove airborne biological material from gas which is exhausted through the outlet openings 34. The filter can be of a known type such as a Mallinckrodt Bar Hydro Baby 355/5427, modified so as to vent radially. Within the generator 6 are two or more series connected venturi devices which produce high levels of vacuum. Details of the vacuum generator 6 need not be shown because they can be of a commercially available type. The vacuum generator 6 can for instance be the same or similar to that disclosed in U.S. Pat. No. 6,394,760, the content of which is incorporated herein by cross-reference. More particularly, the vacuum generator 6 can be commercially available forms of compact vacuum generator known as piINLINE™ MICRO made by Piab AB of Taby Sweden or Vtec VC 102P are suitable for this purpose.

The generator 6 has a vacuum port 36 which is coupled by means of an elbow 38 to the cap 14 of the collecting container assembly 8. The suction tube 10 has a proximal end 42 located within the interior of a container 39 of the assembly 8, as shown. The lower end of the elbow 38 is fitted with a float valve 21 which prevents material collected in the container 39 from entering the vacuum generator 6 in the event that the container becomes overly full. In the illustrated arrangement, the float valve includes a buoyant body 23 of plastics material fitted with a resilient conical valve element 25. The elbow 38 includes a valve seat 27 of complementary shape to the valve element 25. The body 23 and element 25 are slidably located within a housing 29. When the level of the material within the container 39 rises, the valve element 25 will seal against the valve seat 27 to prevent material being sucked into the vacuum generator 6. A one-way valve 45 is mounted at the proximal end 42 of the suction tube 10. The valve 45 prevents syphoning of the contents of the suction tube 10 out of the filter element 46 when the vacuum generator 6 ceases to produce a vacuum. Escape of potentially contaminated material from the suction tube 10 would be undesirable. The suction tube 10 has a straight portion 43 and downwardly inclined distal end portion 44. The elbow 38 and the straight portion 43 of the tube 10 can be held secure by means of a mounting block 41 connected to or formed integrally with the lid 40. The distal end of the portion 44 is fitted with an end filter element 46 which has a number of openings therein to permit air, liquid, mucus and entrained solid particles below a predetermined size to enter the tube 10. The size of the openings in the filter element 46 is such that they do not permit solid bodies of greater size than about 1 mm to 2 mm from entering the tube 10 otherwise larger particles could cause a blockage. In a prototype apparatus, the tube 10 has an external diameter of about 6 millimeters and an internal bore of 5 millimeters. The straight portion 43 has a length of about 75 millimeters whereas the distal portion 44 has a length of about 70 millimeters. The angle between the straight portion 43 and the distal portion 44 is about 150°. The tube can be formed from a relatively rigid plastic material such as ABS, PVC, polycarbonate or polyethylene. The lid 40 and container 39 need to be reasonably robust in order to restrain the internal vacuum when the device is operated. It is preferred that they have a wall thickness in the range from 1 to 2 millimeters, depending on materials, preferably material is polyethylene or polypropylene or any of the materials listed above. It is preferred that the container 39 is transparent so that the operator can inspect the materials collected therein and empty the container 39, if necessary. Being a single use device there is no necessity to empty it as the whole device will normally be disposed of.

The operation of the device is as follows. When suction is required, the operator would place the distal end portion 44 of the device at the location where suction is required typically in the mouth or throat of a patient. The operating lever 24 is then operated. This causes $CO_2$ under high pressure to pass to the vacuum generator 6 causing a vacuum level in the elbow 38 in the range of about −60 kPa to −40 kPa. The interior of the container 39 is therefore under a vacuum level at a similar level to that at the distal end portion 44 of the suction tube. In medical emergency applications, the end of the tube is located in the mouth or throat of the patient and any mucus, blood, vomit or the like is sucked into the tube 10 and collected in the collecting container 39. The operator would normally use the device intermittently as required. Preferably the size of the $CO_2$ cartridge 18 is such that suction is available for a total of about 4 to 15 minutes. Preferably the cartridge 18 has a capacity in the range from 16 to 88 grams and more preferably about 40 grams of liquefied carbon dioxide.

A prototype of the device 2 has been constructed and has been found to perform in a very satisfactory way. In the prototype apparatus, the body assembly 4 and lever 24 and valve 20 were adapted from a commercially available type of dust blower coupled to the vacuum generator 6 in the illustrated device 2.

It is envisaged that in a commercial device, the body assembly 4 and container assembly 8 could be integrally moulded from plastics material as a single body having the necessary elements moulded therein. It is also possible that the housing for the vacuum generator 6 could also be integrally moulded into the same moulding. The wall thicknesses of the moulding would be chosen so as to be able to withstand the positive pressures and vacuum levels which are generated in use and the wall thicknesses would depend on the type of plastics material used. It is preferred that the material would be ABS or polycarbonate and the wall thickness of the assembly 4 would be in the range of say 2.5 to 3 millimeters. It is also envisaged that those parts of the device where the $CO_2$ expands would be made from plastics material which is chosen to have high thermal conductivity so as to enable heat transfer to the expanding $CO_2$ in order to avoid formation of liquid or solid carbon dioxide in those parts of the apparatus in which the $CO_2$ flows.

In the illustrated arrangement, the lower end 45 of the proximal end 42 of the tube is located at a lower level relative to the lower end of the elbow 38. This, as well as the one-way valve 45, minimises the possibility that material collected in the container 39 is sucked into the vacuum generator 6. In the illustrated arrangement, the spacing between the lower ends is about 25 millimeters. In the commercial device the interior of the collection chamber could be moulded with integral baffles to further minimise the possibility of material entering the suction generator and said baffles may also add to the rigidity of such a container to improve its ability to withstand the internal vacuum.

Another arrangement would allow for a flexible catheter to be attached to the mounting block 41 rather than the rigid suction tube 10 to allow removal of mucous and debris from inside or around air patient airway tubes or from within the nasal cavity.

The illustrated device has the further advantage that the container assembly 8 is located upstream of the vacuum generator 6 which again minimises the possibility of unwanted material entering the vacuum generator 6. This contrasts to some known arrangements where the vacuum is created upstream of the collecting container.

It will be appreciated by those skilled in the art that embodiments of the invention can be made so that the device is inexpensive and therefore can be disposable. It is also portable and non-electric. It also does not operate on oxygen supplies which are usually limited and needed for respiration of a patient.

Many modifications will be apparent to those skilled in the art without departing from the spirit and scope of the invention.

LIST OF PARTS portable vacuum device 2
main body assembly 4
vacuum generator 6
collecting container assembly 8
suction tube 10
housing 12
cap 14
pressure chamber 16
cartridge 18
valve 20
float valve 21
outlet port 22
body 23
operating lever 24
valve element 25
pivot pin 26
valve seat 27
operating spindle 28
housing 29
inlet port 30
screw threaded connector 32
filter 33
outlet openings 34
vacuum port 36
elbow 38
container 39
lid 40
mounting block 41
proximal end 42
straight portion 43
downwardly inclined distal end portion 44
one way valve 45
end filter element 46

The invention claimed is:

1. A disposable handheld vacuum device including:
   (i) a body assembly configured to receive a liquid cartridge containing liquid carbon dioxide, an outlet port and a valve for controlling flow, in use, of carbon dioxide gas released from the cartridge to said outlet port;
   (ii) a gas operated vacuum generator having a vacuum inlet port and an exhaust outlet, the inlet port being coupled to receive carbon dioxide gas from said outlet port, the vacuum generator configured to generate a pressure in the range −60 kPa to −40 kPa;
   (iii) a suction tube having proximal and distal ends;
   (iv) a collection container having a container inlet and a container outlet and wherein the container inlet is coupled to the proximal end of the suction tube, the arrangement being such that when said valve is opened the vacuum generator receives unregulated flow of carbon dioxide gas from the cartridge so as to create a vacuum in the container and at the distal end of the suction tube; wherein
   (v) at least those parts of the body assembly where carbon dioxide from the cartridge expands have high thermal conductivity so as to enable heat transfer to the expanding carbon dioxide in order to avoid formation of liquid or solid carbon dioxide.

2. A device as claimed in claim 1 wherein the body assembly includes a pressure chamber within which can be located at least part of the cartridge.

3. A device as claimed in claim 2 wherein the capacity of the cartridge is such that the vacuum generator can be operated for a total time in the range 1 to 15 minutes.

4. A device as claimed in claim 1 wherein the suction tube is rigid or semi-rigid.

5. A device as claimed in claim 1 wherein the suction tube is flexible.

6. A device as claimed in claim 1 wherein a one-way valve is located at the proximal end of the suction tube to prevent flow of material in a direction from the proximal to the distal end of the suction tube.

7. A device as claimed in claim 1 wherein the outlet of the container is in the form of a conduit and wherein a float valve is connected to the conduit, the arrangement being such that when the level of material collected in the container rises to a predetermined point, the float valve closes and prevents flow of material into the outlet of the container.

8. A device as claimed in claim 1 wherein the vacuum generator is coupled to a filter.

9. A device as claimed in claim 8 wherein the filter is capable of removing airborne biological material.

10. A device as claimed in claim 1 wherein the material forming the pressure chamber comprises a thermally conductive plastics material.

11. A method of providing a portable hand-held suction device, the method including the steps of:
    (i) providing a body assembly configured to receive a cartridge containing liquid carbon dioxide;
    (ii) providing a valve for selectively releasing carbon dioxide gas from the cartridge to a vacuum generator configured to generate a pressure in the range −60 kPa to −40 kPa, the valve being operable such that the vacuum generator receives unregulated flow of carbon dioxide gas released from the cartridge;
    (iii) coupling an inlet of the vacuum generator to a container; and
    (iv) providing a suction tube having proximal and distal ends, the proximal end being in fluid communication with the interior of the container whereby a user can selectively operate the valve to release carbon dioxide gas from the canister thereby creating a vacuum in the container and at the distal end of the suction tube; wherein
    (v) at least those parts of the body assembly where carbon dioxide from the cartridge expands have high thermal conductivity so as to enable heat transfer to the expanding carbon dioxide in order to avoid formation of liquid or solid carbon dioxide.

12. A disposable handheld vacuum device according to claim 1, wherein the body assembly is constructed to receive a cartridge having a capacity that does not exceed 88 grams (3.1 oz) of liquid carbon dioxide.

13. A disposable handheld vacuum device according to claim 1, wherein the body assembly is constructed to receive a cartridge having a capacity that does not exceed 40 grams (1.41 oz) of liquid carbon dioxide.

\* \* \* \* \*